United States Patent [19]

Ballany et al.

[11] 4,395,407
[45] Jul. 26, 1983

[54] NOVEL PARASITICIDAL POUR-ON COMPOSITIONS

[75] Inventors: John M. Ballany, Cumbernauld; Andrew R. Galbraith, Glasgow, both of Scotland

[73] Assignee: Janssen Pharmaceutica N.V., Beerse, Belgium

[21] Appl. No.: 365,700

[22] Filed: Apr. 5, 1982

[30] Foreign Application Priority Data

May 8, 1981 [GB] United Kingdom ................. 8114169
Nov. 16, 1981 [GB] United Kingdom ................. 8134406

[51] Int. Cl.³ .................. A61K 31/675; A61K 31/425
[52] U.S. Cl. .................................... 424/200; 424/270
[58] Field of Search ............................... 424/200, 270

[56] References Cited

U.S. PATENT DOCUMENTS 2,767,194 10/1956 Fancher ............................. 260/326
3,274,209 9/1966 Raeymaekers et al. ......... 260/306.7

Primary Examiner—Sam Rosen
Attorney, Agent, or Firm—Geoffrey G. Dellenbaugh

[57] ABSTRACT

The present invention relates to novel stable pour-on compositions for eradicating or controlling parasites in non-human animals, said compositions containing tetramisole and/or levamisole and an organophosphate along with an acid to improve the efficiency of the composition.

19 Claims, No Drawings

NOVEL PARASITICIDAL POUR-ON COMPOSITIONS

DESCRIPTION OF THE INVENTION

Warm-blooded non-human animals, more especially, sheep and cattle, which are valuable sources of meat, skins, fur, wool or similar fabric materials are subject to infestation by parasites, endo- and/or ecto-parasites, which feed off their host and cause irritation resulting in a reduction of the quantity and/or the quality of said meat, skins, fur, wool or similar fabric material.

Under certain environmental conditions, such animals may be attacked by both endoparasites, for example, helminths such as gut and lungworms, and ectoparasites, for example, lice, keds, mites, ticks and fleas.

Various chemical compounds are used to eradicate and/or to interfere with the development and/or the reproduction of said parasites. Most parasiticidal compounds have a rather selective activity: some compounds have ectoparasiticidal activity while other compounds have endoparasiticidal activity.

An important group of ectoparasiticidal compounds are the organophosphates, having the functional group

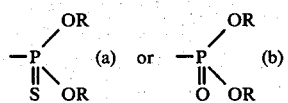

wherein R is $C_1$–$C_6$ lower alkyl, which compounds have been described in U.S. Pat. No. 2,767,194. One of the most active ectoparasitical compounds in this group is phosmet, having the formula

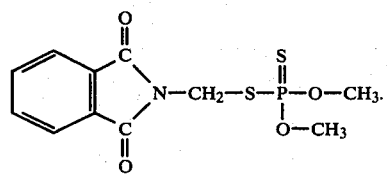

One particularly effective endoparasiticidal, and more particularly, anthelmintic, compound is tetramisole, being chemically designated as 2,3,5,6-tetrahydro-6-phenylimidazo[2,1-b]thiazole, and its laevo isomer, levamisole, which are described in British Pat. No. 1,043,489 and which are represented by the formula

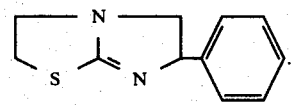

These endo- and ectoparasiticidal compounds may be administered in the oral-, parenteral- or topical way depending upon the the parasiticidal compounds, the compositions which comprise these compounds and the nature of the parasites. A particularly preferred administration route is the pour-on administration, which combines several advantages such as accuracy and ease of application, whereby the active ingredient in a carrier or a solvent is applied to a specific skin region of an animal by pouring on the formulation or applying small discrete amounts of spots. The preferred area is along the back of the animal.

While as well tetramisole or levamisole as phosmet may be administered in a pour-on administration way, we surprisingly found that, in comparison with pour-on compositions comprising separately tetramisole/levamisole and phosmet, the pour-on compositions comprising a mixture of tetramisole/levamisole and phosmet in a suitable carrier or solvent are less effective when administered to warm-blooded animals.

Chemical analysis procedures show that pour-on or spot-on compositions comprising a mixture of tetramisole/levamisole and phosmet contain a certain amount of the complex formed by tetramisole/levamisole and phosmet.

The present invention relates to a novel pour-on composition for eradicating or controlling parasites in non-human animals, which composition comprises
  (a) from 1 to 30% by weight of tetramisole and/or levamisole;
  (b) from 2 to 15% by weight of phosmet; and
  (c) one or more optionally substituted aliphatic carboxylic acids, having each a $pK_a$-value comprised between 0.6 and 6, in a molar excess of 1.5:1 to 12:1 over tetramisole and/or levamisole
in a suitable solvent and/or carrier, said composition having a high degree of stability and having unimpaired efficacy against parasites in non-human animals.

The term "parasites" is meant to include ectoparasites, such as, for example, helminths and the like, as well as endoparasites, such as, for example, lice, keds, mites, ticks, fleas and the like.

The term "controlling parasites" is meant to include the interference with the development and/or the reproduction of said parasites.

The term "unimpaired efficacy" means that the compositions of the present invention have an efficacy which is unimpaired in comparison with the efficacy of two compositions comprising the same amount of tetramisole and/or levamisole and phosmet separately.

As used in the foregoing definitions the $pK_a$-value has the meaning of $-\log K_a$, wherein $K_a$ is the dissociation constant of the most acidic function of the molecule at 25° C. in aqueous medium.

Preferred compositions are those comprising for 1 to 10% by weight of tetramisole and/or levamisole and from 2 to 15% by weight of phosmet.

Particularly preferred compositions are those comprising from 3 to 7% by weight of tetramisole and/or levamisole and from 5 to 12% by weight of phosmet.

More particularly preferred compositions are those comprising from 3 to 7% by weight of levamisole and from 5 to 12% by weight of phosmet.

Suitable optionally substituted aliphatic carboxylic acids are, for example, formic acid, acetic acid, propionic acid, trichloroacetic acid, citric acid, lactic acid, malonic acid and the like.

The selection of the optionally substituted aliphatic carboxylic acids is limited by the desired high degree of stability of the composition and by the requirement that the composition may not be irritative. Compositions which combine said high degree of stability and lack of skin-irritations are those comprising at least one member selected from the group consisting of acetic acid, citric acid, formic acid, trichloroacetic acid and malonic acid.

More especially preferred compositions are those comprising from 1 to 10% by weight of acetic acid and from 5 to 15% by weight of citric acid.

Suitable solvents and/or carriers, combining a good skin-penetration with a lack of skin-irritation, comprise at least 50% by weight of a solvent consisting of one or more alcohols, having the formula $$HO-(CH_2-CH_2-O)_m-R \qquad (III)$$

wherein m is the integer 1, 2 or 3; and R is lower alkyl.

As used in the foregoing definition the term lower alkyl is meant to include straight and branched hydrocarbon radicals having from 1 to 6 carbon atoms such as, for example, methyl, ethyl, 1-methylethyl, 1,1-dimethylethyl, propyl, 2-methylpropyl, butyl, pentyl, hexyl and the like.

Suitable alcohols of formula (III) are, for example, 2-methoxyethanol, 2-(2-ethoxyethoxy)ethanol, 2-(2-butoxyethoxy)ethanol and the like.

The alcohols of formula (III) wherein m is 2 combine a good penetration capacity with a relatively high flashpoint, thus enhancing the safety margin, and therefor these alcohols are especially preferred.

Due to its excellent spreading and run-off properties 2-(2-butoxyethoxy)ethanol is the most preferred alcohol.

The amount of the alcohol or alcohols of formula (III) in the medium may vary within rather wide limits, from 50% to 100% by weight of the medium. It has however been found that the incidence of skin irritation shows a tendency to decrease with an increasing content of said alcohol or alcohols. Compositions wherein the medium comprises at least 80% by weight of one or more alcohols of formula (III) are therefor preferred.

Particularly preferred are compositions wherein the medium consists essentially of one or more of said alcohols.

The most preferred compositions are those wherein the medium consists essentially of 2-(2-butoxyethoxy)ethanol.

The compositions of the present invention may contain additives of any nature in minor proportions, which additives do not introduce a significant deleterious effect on the skin. Said additives may facilitate the administration to the skin of the animals and/or may be helpful for preparing the desired compositions. Some examples of additives are cited hereinafter.

Minor amounts of aliphatic hydrocarbon mixtures may reduce the surface tension of the compositions and, as such, said aliphatic hydrocarbon mixtures may prevent an excessive adhesion of the applied compositions to the hair and facilitate their spreading over the skin, resulting in an enhanced resorption of the anthelmintic by the skin.

The presence of minor amounts of one or more dipolar aprotic solvents may enhance the penetration rate of the compositions. Suitable dipolar aprotic solvents are, for example, N,N-dimethylformamide, N,N-dimethylacetamide, dimethyl sulfoxide, N-methyl-2-pyrrolidone and the like.

The compositions may also contain other additives such as, for example, substances the taste of which deters animals from licking the applied compositions off the animals treated, pigments making it possible to recognize the treated animals and the like.

The parasiticidal compounds may be administered within a range of 0.1 to 500 mg/kg of body weight and a preferred range is between 1 and 50 mg levamisole per kg of body weight and between 2 and 100 mg phosmet per kg of body weight.

In formulations according to the present invention the individual active ingredients work with unimpaired efficiency within one pour-on composition for controlling animal parasites.

The compositions of the present inventions may be prepared by intimately admixing the desired components in a suitable manner.

Although the hereinabove described compositions are useful for combating parasites in all non-human animals, in general they are especially preferred for the treatment of cattle and sheep.

The hereinafter described examples are illustrative for the stability of the compositions of the present invention. These examples are intended to illustrate and not to limit the scope of the present invention.

EXAMPLE I

A solution of levamisole in carbon tetrachloride was mixed with a suspension of PHOSMET in the same solvent. On admixture the phosmet particles rapidly dissolved and after a period of time, an oily material separated from the solution. It was not possible to quantitatively recover the levamisole or phosmet by either high pressure liquid chromatography HPLC or gas pressure liquid chromatography GPLC. The mass spectrograph of the oily liquid produced a new peak at molecular weight 473 indicating a possible 1:1 complex.

EXAMPLE II

A solution of levamisole in 2-(2-butoxyethoxy)ethanol was mixed with a solution of phosmet in the same solvent. There was no visible evidence of reaction. It was not possible to quantitatively recover the levamisole or phosmet by HPLC OR GPLC. The mass spectrograph of the solution produce a new peak at molecular weight 473 indicating a possible 1:1 complex.

EXAMPLE III

Levamisole (5 g) was dissolved in 2-(2-butoxyethoxy)ethanol (72 g) and then citric acid (10 g) and glacial acetic acid (5 g) were added to the solution. Phosmet (10 g) was subsequently added to the solution and dissolved therein, to produce an acidic solution of 102 g/100 mg composition.

The resulting solution was analysed by HPLC and GPLC and gave quantitative recovery of both levamisole and phosmet after a time period of 4 months with no trace of inter-reaction.

Other solvents or acids may be utilized in the mixture to provide equivalent stability. The above choice of acids and solvents ensures that the levamisole and phosmet are in a suitable form for administering to an animal's skin and simultaneously allow (i) efficacy against both endo- and ecto-parasites, (ii) safe application to the infested animal, (iii) no local irritation of the animals's skin and (iv) improved absorbtion of levamisole.

EXAMPLE IV

Levamisole (5 g) was dissolved in 2-(2-butoxyethoxy)ethanol (80 g) and then malonic acid (5 g) was dissolved into the solution. Phosmet (10 g) was subsequently added to the solution, and dissolved therein, to produce an acidic solution of 100 g/100 ml composition.

What is claimed is:

1. A pour-on or spot-on composition for eradicating or controlling parasites in non-human animals, said compositions comprising
   (a) from 1 to 30% by weight of tetramisole and/or levamisole;
   (b) from 2 to 15% by weight of phosmet; and
   (c) one or more optionally substituted aliphatic carboxylic acids, having each a $pK_a$-value comprised between 0.6 and 6 in a molar excess of 1.5:1 to 12:1 over tetramisole and/or levamisole
in a suitable solvent and/or carrier.

2. A composition according to claim 1 wherein the amount of tetramisole and/or levamisole is comprised between 1 and 10% by weight and the amount of phosmet is comprised between 2 and 15% by weight.

3. A composition according to claim 1 wherein the amount of tetramisole and/or levamisole is comprised between 3 and 7% by weight of tetramisole and/or levamisole and from 5 to 12% by weight of phosmet.

4. A composition according to claim 1 comprising from 3 to 7% by weight of levamisole and from 5 to 12% by weight of phosmet.

5. A pour-on or spot-on composition according to claim 1 for eradicating or controlling parasites in non-human animals, said composition comprising
   (a) from 1 to 30% by weight of tetramisole and/or levamisole;
   (b) from 2 to 15% by weight of phosmet; and
   (c) at least one member selected from the group consisting of acetic acid, citric acid, formic acid, trichloroacetic acid and malonic acid in a suitable solvent and/or carrier.

6. A composition according to claim 5 comprising from 1 to 10% by weight of actic acid and from 5 to 15% by weight of citric acid.

7. A pour-on or spot-on composition for eradicating or controlling parasites in non-human animals, said composition comprising
   (a) from 3 to 7% by weight of levamisole;
   (b) from 5 to 12% by weight of phosmet;
   (c) from 1 to 10% by weight of acetic acid; and
   (d) from 5 to 15% by weight of citric acid
in a suitable solvent and/or carrier.

8. A pour-on or spot-on composition for eradicating or controlling parasites in non-human animals, said composition comprising
   (a) from 10 to 30% by weight of tetramisole and/or levamisole;
   (b) from 2 to 15% by weight of phosmet; and
   (c) one or more optionally substituted aliphatic carboxylic acids, having each a $pK_a$-value comprised between 0.6 and 6 in a molar excess of 1.5:1 to 12:1 over tetramisole and/or levamisole.
in a medium comprising at least 50% by weight of a solvent and/or carrier consisting of one or more alcohols, having the formula $$HO-(CH_2-CH_2-O)_m-R \qquad (III)$$

wherein m is the integer 1, 2 or 3; and R is lower alkyl.

9. A composition according to claim 8 wherein the medium comprises at least 80% by weight of a solvent and/or carrier of formula (III).

10. A composition according to claim 8 wherein the medium consists essentially of one or more alcohols of formula (III).

11. A pour-on or spot-on composition for eradicating or controlling parasites in non-human animals, said composition comprising
    (a) from 10 to 30% by weight of tetramisole and/or levamisole;
    (b) from 2 to 15% by weight of phosmet; and
    (c) one or more optionally substituted aliphatic carboxylic acids, having each a $pK_a$-value comprised between 0.6 and 6 in a molar excess of 1.5:1 to 12:1 over tetramisole and/or levamisole
in a medium comprising at least 50% by weight of a solvent and/or carrier consisting of one or more alcohols having the formula $$HO-(CH_2-CH_2-O)_2-R \qquad (III\text{-}a)$$

wherein R is lower alkyl.

12. A composition according to claim 11 wherein the medium comprises at least 80% by weight of a solvent and/or carrier of formula (III-2).

13. A composition according to claim 11 wherein the medium consists essentially of one or more alcohols of formula (III-2).

14. A pour-on or spot-on composition for eradicating or controlling parasites in non-human animals, said composition comprising
    (a) from 10 to 30% by weight of tetramisole and/or levamisole;
    (b) from 2 to 15% by weight of phosmet; and
    (c) one or more optionally substituted aliphatic carboxylic acids, having each a $pK_a$-value comprised between 0.6 and 6 in a molar excess of 1.5:1 to 12:1 over tetramisole and/or levamisole.
in a medium comprising at least 50% by weight of 2-(2-butoxyethoxy)-ethanol.

15. A composition according to claim 14 wherein the medium comprises at least 80% of 2-(2-butoxyethoxy)ethanol.

16. A composition according to claim 14 wherein the medium consists essentially of 2-(2-butoxyethoxy)ethanol.

17. A pour-on or spot-on composition for eradicating or controlling parasites in non-human animals, said composition comprising
    (a) from 3 to 7% by weight of levamisole;
    (b) from 5 to 12% by weight of phosmet;
    (c) from 1 to 10% by weight of acetic acid; and
    (d) from 5 to 15% by weight of citric acid
in a medium comprising at least 50% by weight of 2-(2-butoxyethoxy)ethanol.

18. A composition according to claim 17 wherein the medium comprises at least 80% of 2-(2-butoxyethoxy)ethanol.

19. A composition according to claim 17 wherein the medium consists essentially of 2-(2-butoxyethoxy)ethanol.

* * * * *